US008639336B2

(12) United States Patent
Bornzin et al.

(10) Patent No.: US 8,639,336 B2
(45) Date of Patent: Jan. 28, 2014

(54) SYSTEM AND METHOD FOR DETECTING AND CORRECTING ATRIAL UNDERSENSING

(71) Applicant: Pacesetter, Inc., Sylmar, CA (US)

(72) Inventors: Gene A. Bornzin, Simi Valley, CA (US);
Peter Boileau, Valencia, CA (US);
Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/662,091

(22) Filed: Oct. 26, 2012

(65) Prior Publication Data

US 2013/0053714 A1     Feb. 28, 2013

Related U.S. Application Data

(62) Division of application No. 11/549,494, filed on Oct. 13, 2006, now Pat. No. 8,321,020.

(51) Int. Cl.
*A61N 1/362*     (2006.01)

(52) U.S. Cl.
USPC .................................. 607/27; 607/9; 607/11

(58) Field of Classification Search
USPC ................. 607/4, 9, 11, 27–28; 600/508–510
See application file for complete search history.

(56) References Cited

U.S. PATENT DOCUMENTS

| 5,144,949 | A | | 9/1992 | Olson | |
|---|---|---|---|---|---|
| 5,725,561 | A | * | 3/1998 | Stroebel et al. | 607/9 |
| 6,112,119 | A | * | 8/2000 | Schuelke et al. | 607/9 |
| 6,129,745 | A | * | 10/2000 | Sun et al. | 607/27 |
| 6,594,523 | B1 | | 7/2003 | Levine | |
| 7,065,398 | B2 | | 6/2006 | Hettrick et al. | |
| 2003/0069611 | A1 | * | 4/2003 | Levine | 607/27 |

FOREIGN PATENT DOCUMENTS

WO     2004028364 A1     4/2004

OTHER PUBLICATIONS

NonFinal Office Action, mailed Nov. 10, 2008—U.S. Appl. No. 11/549,494.
Restriction Requirement, mailed Apr. 3, 2009—U.S. Appl. No. 11/549,494.
NonFinal Office Action, mailed Aug. 31, 2009—U.S. Appl. No. 11/549,494.
NonFinal Office Action, mailed Mar. 30, 2010—U.S. Appl. No. 11/549,494.
Final Office Action, mailed Feb. 1, 2011—U.S. Appl. No. 11/549,494.
Advisory Action, mailed Apr. 11, 2011—U.S. Appl. No. 11/549,494.
Notice of Allowance, mailed Aug. 3, 2012—U.S. Appl. No. 11/549,494.

* cited by examiner

*Primary Examiner* — Rex R Holmes

(57) ABSTRACT

A method for operating an implantable medical device includes delivering a plurality of pacing pulses to an atria of a patient's heart and monitoring intrinsic atrial activity to detect intrinsic atrial contractions between one or more of the plurality of pacing pulses. The method further includes detecting atrial undersensing as a function of the detection of intrinsic atrial contractions.

7 Claims, 12 Drawing Sheets

SYSTEM AND METHOD FOR DETECTING AND CORRECTING ATRIAL UNDERSENSING

CROSS REFERENCE TO RELATED APPLICATIONS

This application is a divisional of U.S. patent application Ser. No. 11/549,494, filed Oct. 13, 2006, now U.S. Pat. No. 8,321,020.

FIELD OF THE INVENTION

This invention generally relates to programmable cardiac stimulating devices and more particularly relates to implantable stimulation devices and associated methods for automatically detecting and correcting the undersensing of atrial waves.

BACKGROUND

In a normal human heart, the sinus node, generally located near the junction of the superior vena cava and the right atrium, constitutes the primary natural pacemaker initiating rhythmic electrical excitation of the heart chambers. A cardiac impulse arising from the sinus node is conducted to the atrial chambers, causing a depolarization known as a P-wave and a corresponding contraction of the atrial chambers. The excitation pulse is further transmitted to and through the ventricles via the atrioventricular (A-V) node and a ventricular conduction system causing a depolarization known as an R-wave and a corresponding contraction of the ventricular chambers.

Disruption of this natural pace-making and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. Stimulation may be delivered to the atrial and/or the ventricular heart chambers depending on the location and severity of the conduction disorder.

In a dual chamber, demand-type pacemaker, commonly referred to as DDD pacemaker, an atrial channel and a ventricular channel each include a sense amplifier to detect cardiac activity in the respective chamber and an output circuit for delivering stimulation pulses to the respective chamber. If the atrial channel does not detect an intrinsic atrial depolarization signal (a P-wave), a stimulating pulse will be delivered to depolarize the atrium and cause contraction. Following either a detected P-wave or an atrial pacing pulse, the ventricular channel attempts to detect a depolarization signal in the ventricle. If no R-wave is detected within a defined atrial-ventricular interval (AV interval or delay), a stimulation pulse is delivered to the ventricle to cause a ventricular contraction. In this way, atrial-ventricular synchrony is maintained by coordinating the delivery of ventricular output in response to a sensed or paced atrial event.

In dual chamber stimulation devices, therefore, accurate sensing of evoked responses and the intrinsic deflection of the naturally occurring cardiac events, also referred to as "intrinsic" events, is crucial for achieving atrial-ventricular synchrony and for other desired functions, such as mode switching and the like. Therefore, atrial undersensing, i.e., the failure to sense intrinsic atrial depolarization signals can seriously compromise atrial-ventricular synchrony. Atrial undersensing may arise from a number of different sources, including, by way of example, the patient's activity level, atrial lead dislodgment, improper atrial sensitivity setting, or variations in P-wave amplitude induced by respiration.

While many techniques have been incorporated into dual chamber pacemaker technology to improved atrial sensing reliability, the occurrence of undersensing remains a problem that continues to compromise the performance of many implanted device. For example, atrial fibrillation is often not detected as a result of undersensing intrinsic activity in the atrium. Failing to detect atrial fibrillation typically does not cause discomfort for the patient because the high rate atrial tachycardia is not tracked and the pacemaker does not go to the maximum track rate and thus overdrive the ventricle at an elevated rate. However atrial fibrillation is a serious problem and can result in stroke if not recognized or treated with anticoagulant drugs.

SUMMARY

In accordance with one aspect of the present invention a method for operating an implantable medical device includes delivering a plurality of pacing pulses to the atria of a patient's heart and detecting atrial undersensing as a function of the detection of intrinsic atrial contractions between one or more of the plurality of pacing pulses.

In another aspect of the present invention a method for operating an implantable medical device includes detecting atrial undersensing as a function of intrinsic atrial electrical activity and confirming detection of atrial undersensing as a function of intrinsic ventricular electrical activity.

In a further aspect of the present invention a method for operating an implantable medical device includes detecting atrial undersensing as a function of detection of intrinsic atrial electrical activity when pacing with a first set of pacing parameters and then adjusting one or more of the pacing parameters in the first set. In accordance with this aspect of the present invention the detection of atrial undersensing is then confirmed as a function of detection of intrinsic atrial electrical activity while pacing in accordance with the adjusted pacing parameters.

In a still further aspect of the present invention a method for operating an implantable medical device includes monitoring a number of automatic mode switches from a tracking pacing mode to a non-tracking pacing mode and detecting atrial undersensing as a function of the number of automatic mode switches.

In another aspect of the present invention an implantable medical device includes a pulse generator adapted to deliver a plurality of pacing pulses to the atria of a patient's heart in accordance with a first pacing rate. The implantable medical device further includes a microcontroller adapted to monitor intrinsic atrial activity to detect intrinsic atrial contractions between one or more of the plurality of pacing pulses the microcontroller being further adapted to detect atrial undersensing as a function of the detection of intrinsic atrial contractions.

BRIEF DESCRIPTION OF THE DRAWINGS

Further features and advantages may be more readily understood by reference to the following description taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

In one embodiment of the present invention an implantable stimulation device monitors the patient for atrial undersensing and automatically adjusts one or more operating parameters of the implantable device to eliminate device undersensing. The present invention may be implemented in connection with any stimulation device that is configured or configurable to monitor intrinsic electrical cardiac activity. However, the advantages of the present invention may be best understood in connection with an exemplary stimulation device that is capable of being used in connection with the various embodiments that are described below.

It is to be appreciated and understood that other stimulation devices, including those that are not necessarily implantable, can be used and that the description below is given, in its specific context, to assist the reader in understanding, with more clarity, the inventive embodiments described herein. In the description that follows, like numerals or reference designators will be used to refer to like parts or elements throughout.

Figure 1:
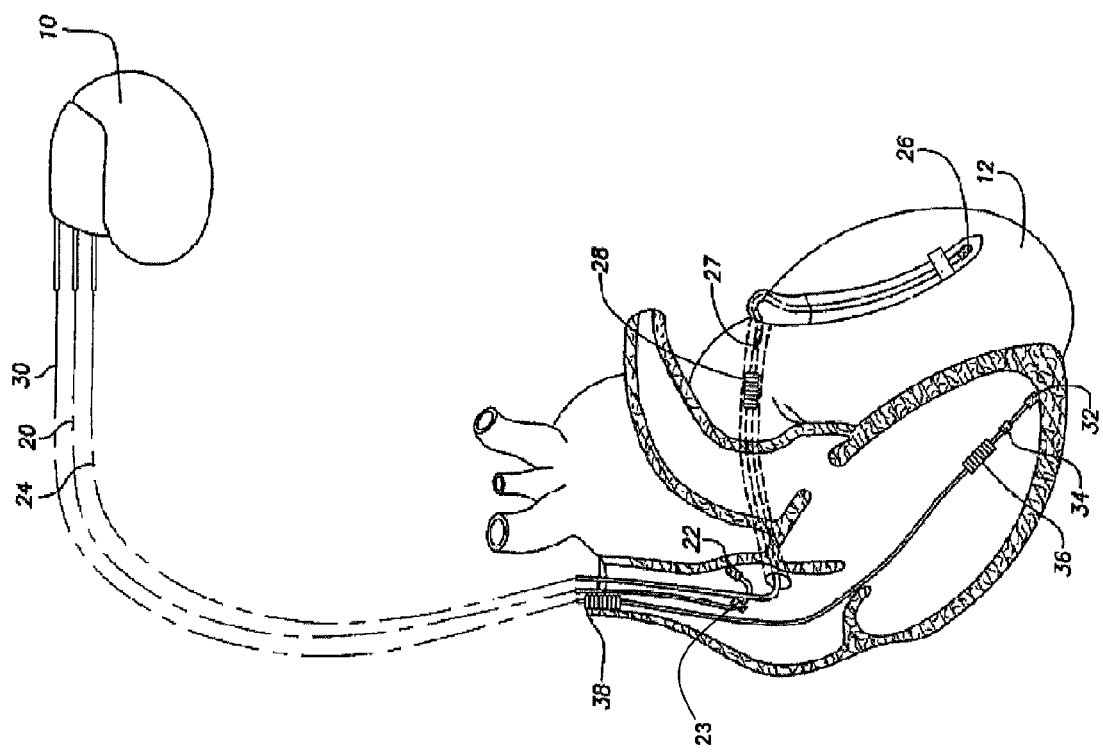
FIG. 1 is a simplified diagram of one embodiment of an implantable stimulation device in electrical communication with a patient's heart for delivering multi-chamber stimulation and shock therapy in accordance with one embodiment of the present invention.

FIG. 1 illustrates a prophylactic defibrillation and stimulation device 10 (also referred to herein as a prophylactic pacer/defibrillator) in electrical communication with a heart 12 by way of three leads 20, 24 and 30, suitable for delivering multi-chamber pacing stimulation therapy and ventricular defibrillation shock therapy. To sense atrial cardiac signals and to provide right atrial chamber stimulation therapy, device 10 is coupled to an implantable right atrial lead 20 having at least an atrial tip electrode 22 and an atrial ring electrode 23, which typically is implanted in the right atrial appendage.

To sense left atrial and ventricular cardiac signals and to provide left chamber pacing therapy, stimulation device 10 is coupled to a coronary sinus lead 24 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 10 is also shown in electrical communication with the patient's heart 12 by way of an implantable right ventricular lead 30 having, in this implementation, a right ventricular tip electrode 32, a right ventricular ring electrode 34, a right ventricular (RV) coil electrode 36 (or other electrode capable of delivering a shock), and superior vena cava (SVC) coil electrode 38 (or other electrode capable of delivering a shock). Typically, the right ventricular lead 30 is transvenously inserted into the heart 12 to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of sensing or receiving cardiac signals, and delivering stimulation in the form of pacing and shock therapy to the right ventricle.

Figure 2:
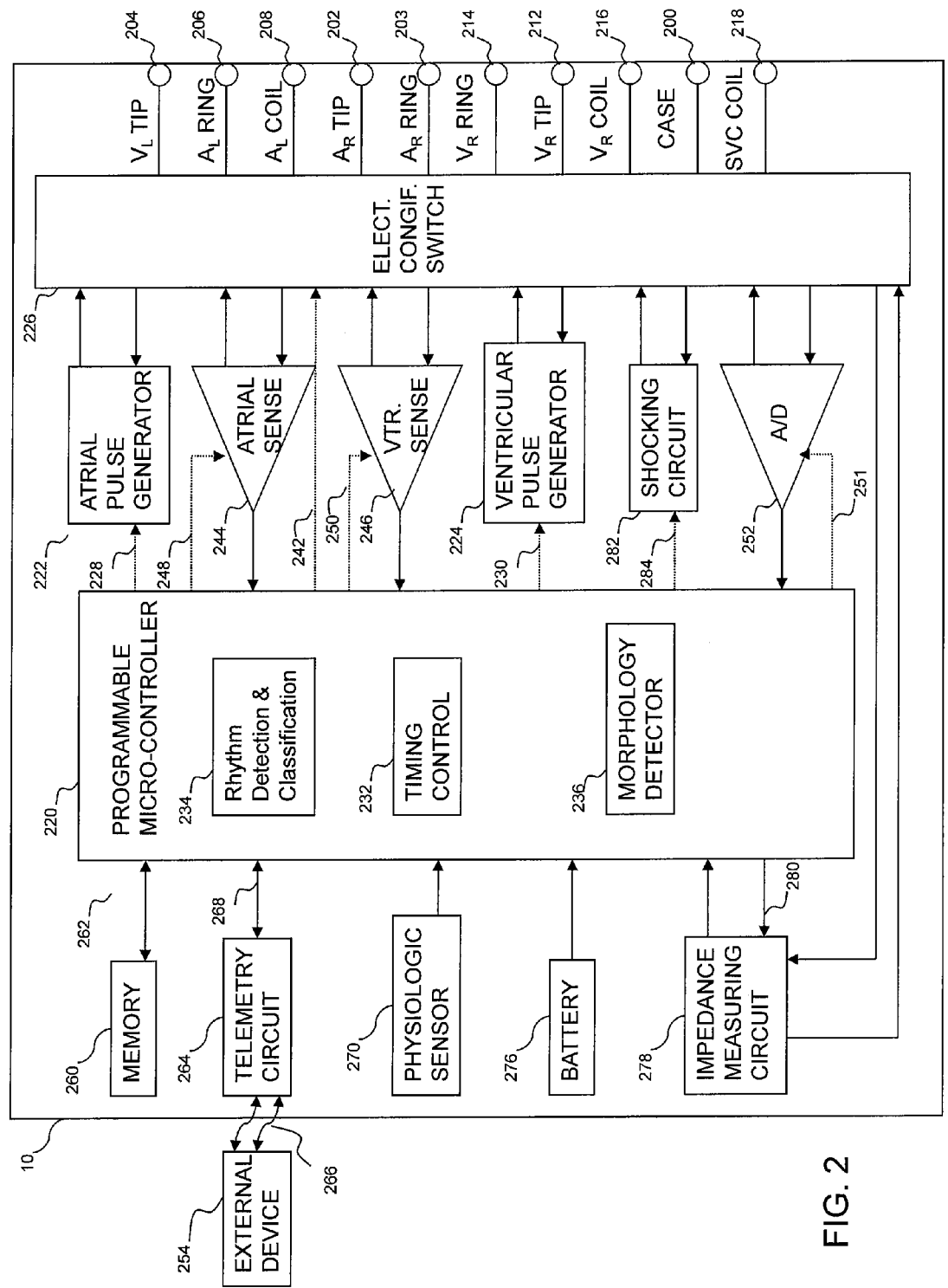
FIG. 2 is a simplified block diagram of a multi-chamber implantable stimulation device configured to provide cardioversion, defibrillation or pacing stimulation or any combination thereof in accordance with one embodiment of the present invention.

FIG. 2 shows an exemplary, simplified block diagram depicting various components of stimulation device 10. The stimulation device 10 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 10 is often referred to as the "can", "case" or "case electrode", and may be selected to act as the return electrode for all "unipolar" modes. Housing 200 may further be used as a return electrode alone or in combination with one or more of the coil electrodes 28, 36 or 38 for shocking purposes. Housing 200 further includes a connector (not shown) having a plurality of terminals 202, 203, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 22. A right atrial ring terminal (AR RING) 203 may also be included adapted for connection to the atrial ring electrode 23. To achieve left chamber sensing, pacing, and shocking, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 26, the left atrial ring electrode 27, and the left atrial coil electrode 28, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 20, the coronary sinus lead 24, and/or the right ventricular lead 30 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 220 is further coupled to a memory 260 by a suitable data/address bus 262, wherein the programmable operating parameters used by the microcontroller 220 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 10 may be non-invasively programmed into the memory 260 through a telemetry circuit 264 in telemetric communication via communication link 266 with an external device 254, such as a programmer, trans-telephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 10 (as contained in the microcontroller 220 or memory 260) to be sent to the external device 254 through an established communication link 266.

The stimulation device 10 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 10, it is to be understood that the physiologic sensor 270 may also be external to the stimulation device 10, yet still be implanted within or carried by the patient.

Examples of physiologic sensors that may be implemented in device 10 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 10, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 10 may employ lithium/silver vanadium oxide batteries.

The stimulation device 10 can further include magnet detection circuitry (not shown), coupled to the microcontroller 220, to detect when a magnet is placed over the stimulation device 10. A magnet may be used by a clinician to perform various test functions of the stimulation device 10 and/or to signal the microcontroller 220 that the external programmer 254 is in place to receive or transmit data to the microcontroller 220 through the telemetry circuits 264.

The stimulation device 10 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 20, the coronary sinus lead 24, and the right ventricular lead 30 through the switch 226 to sample cardiac signals across any pair of desired electrodes.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 10 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 20, coronary sinus lead 24, and the right ventricular lead 30, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations.

The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 10 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

In the case where the stimulation device 10 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220.

Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 200 may act as an active electrode in combination with the RV coil electrode 36, and/or as part of a split electrical vector using the SVC coil electrode 38 or the left atrial coil electrode 28 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

However, arrhythmia detection and control is complicated by problems which are inherent in accurately detecting intrinsic cardiac events. For example, sensing far-field R-waves can result in "oversensing" of intrinsic atrial events (i.e. P-waves). A far-field R-wave is a signal induced on an atrial electrode by global electrical field changes that result from a ventricular depolarization. Because the mass of ventricular myocardium is much larger than the mass of atrial myocardium, the amplitude of a far-field R-wave may be comparable in amplitude to the near-field signal produced by an atrial depolarization.

The term "oversensing" implies that a threshold is set too low. However it may be difficult in some cases to select a threshold for the atrial sensing channel which is high enough to reject far-field R-waves and also low enough to reliably sense P-waves (i.e. does not under-sense intrinsic atrial activity). In addition, the amplitude of events occurring during atrial or ventricular fibrillation is typically much smaller than that of P-waves and R-waves produced during normal impulse conduction. Therefore, a fixed sensing threshold appropriate for reliably sensing P-waves or R-waves which occur during a normal sinus rhythm may result in undersensing of intrinsic activity during atrial or ventricular fibrillation.

Therefore, in one embodiment, the stimulation device employs, by way of example, one or more refractory periods and blanking periods to prevent the misidentification of electrical events and to more accurately detect the intrinsic heart rate. Within a refractory period, the implantable device does not process intrinsic electrical signals during a predetermined interval of time—either for all device functions (an absolute refractory period) or for selected device functions (a relative refractory period).

Figure 3:
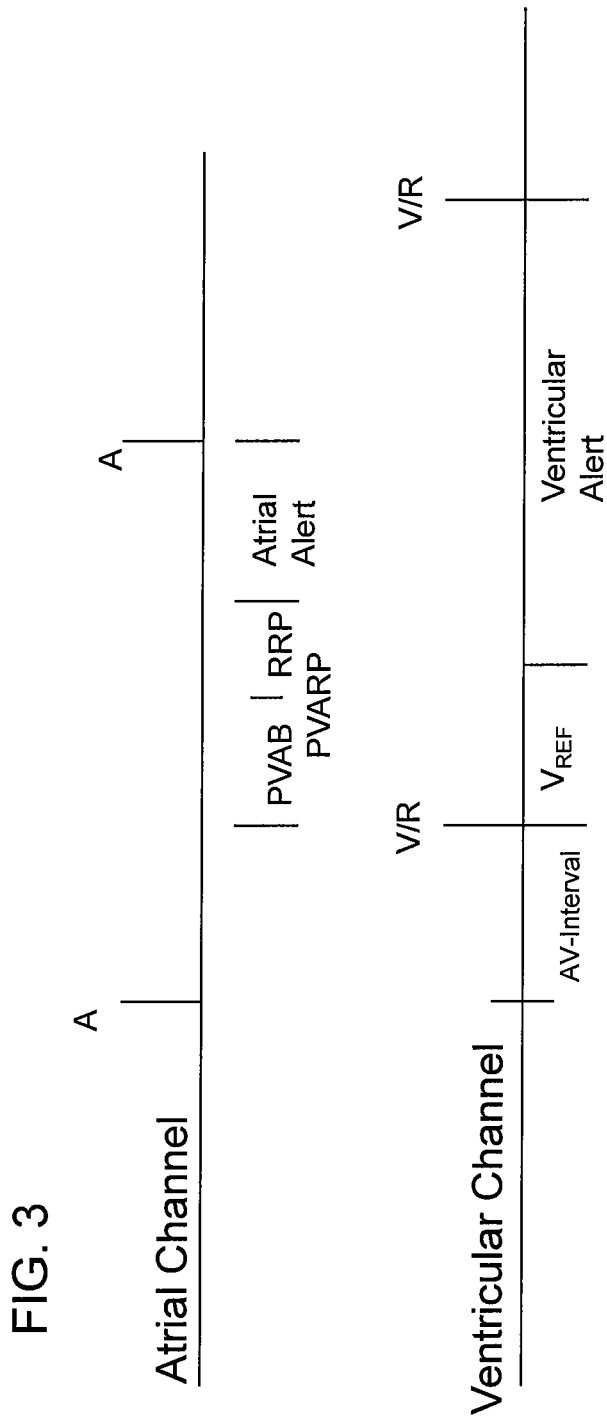
FIG. 3 is a timing diagram illustrated cardiac electrical activity on an atrial channel and a ventricular channel.

For example, as illustrated in the timing diagram of FIG. 3, a microcontroller, in accordance with one embodiment, monitors the ventricular channel after a paced or intrinsic atrial contraction to detect a depolarization signal in the ventricle, known as an R-wave. If an R-wave is not detected within a defined atrial-ventricular interval (AV interval, also referred to as AV delay), a stimulation pulse is delivered to the ventricle to cause ventricular depolarization. In this way, rhythmic dual chamber pacing is achieved by coordinating the delivery of ventricular output in response to a sensed or paced atrial event.

In one embodiment the stimulation device employs a ventricular refractory period ($V_{REF}$) which is initiated by the onset of the ventricular stimulation pulse (or the sensing of an R-wave). All ventricular events occurring during the $V_{REF}$ period are neither sensed nor tracked. In some instances a ventricular alert period follows the ventricular refractory period during which electrical signals on the ventricular channel are detected and tracked.

The onset of the ventricular stimulation pulse (or the sensing of an R-wave) on a ventricular sensing channel also initiates a Post-Ventricular Atrial Refractory Period (PVARP) on an atrial sensing channel. A first portion of the PVARP comprises a post ventricular atrial blanking (PVAB) interval wherein the pacemaker can detect signals on the atrial channel but typically does not use the signals for most purposes. Usually, when the implantable medical device 10 is operating in a dual chamber tracking mode (i.e. DDD), PVARP is longer than $V_{REF}$ to prevent the sensing of an R-wave on an atrial channel.

The PVAB is provided to prevent the device from erroneously responding to a far-field R-wave on the atrial channel. The PVARP concludes with a relative refractory period (RRP) during which the pacemaker continues to ignore all signals detected on the atrial channel as far as the triggering or inhibiting of pacing functions is concerned, but not for other functions, such as detecting rapid atrial rates or recording diagnostic information.

While the use of refractory periods is beneficial in improving the detection and classification of intrinsic electrical activity, they alone may not be suitable for all patients and all circumstances. For example, following the ventricular event, the device times out the PVAB interval during which the atrial detection circuitry is rendered inactive and does not detect atrial activity. However, if the PVAB interval is programmed with a value that is too long from a physiological standpoint, a P-wave that occurs relatively rapidly after the R-wave because of a high intrinsic heart rate will not be detected by the atrial detection circuitry.

Nevertheless, an immediately following R-wave which occurs in the ventricular alert interval is detected and registers as a ventricular event on the ventricular channel. This cycle continues, with the device's atrial detection ability lost or compromised due to the length of the PVAB interval. In some cases, the device may erroneously treat the R-waves as premature ventricular contractions (PVC), which in turn may lead to the delivery of inappropriate therapy by the device.

Therefore, one embodiment of an implantable medical device includes the ability to detect and document episodes of atrial-undersensing for later use as diagnostic information. In some embodiments, the present invention also automatically adjusts one or more operating parameters of the implantable medical device to correct for undersensing.

One of skill in the art will appreciate that the present invention is not limited to particular pacing modes or those that include blanking intervals. Further, the present invention may be implemented using any known technique for sensing cardiac electrical activity including morphology discrimination, frequency analysis or the like.

Figure 4:
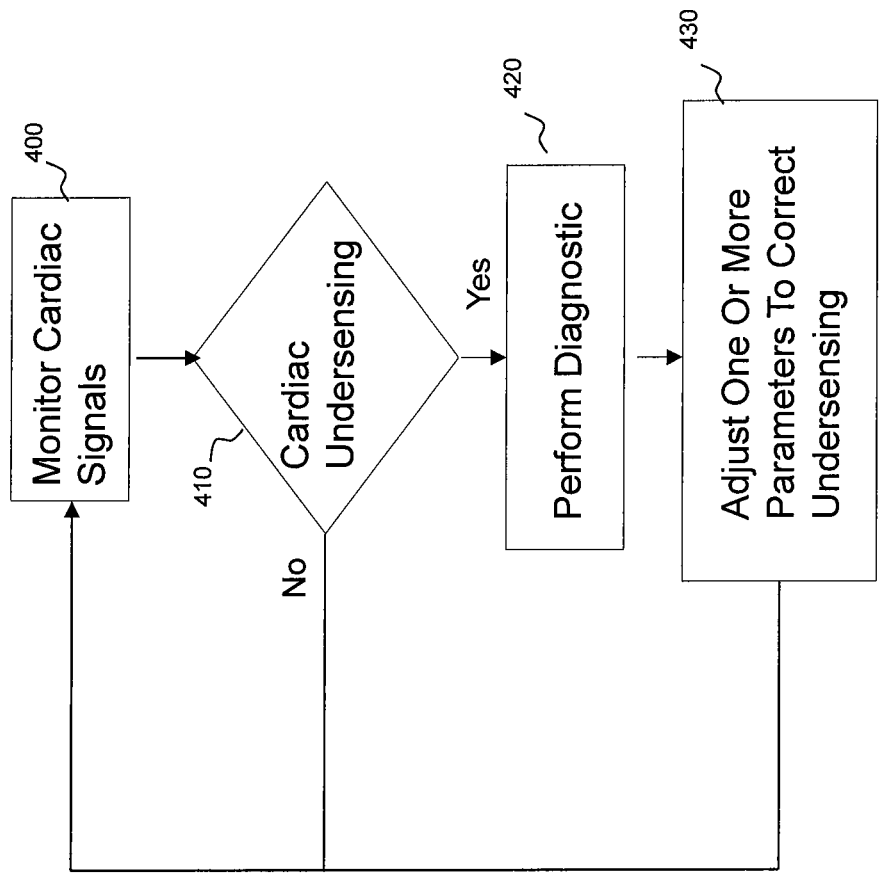
FIG. 4 is a flow chart illustrating a method to detect atrial undersensing in accordance with one embodiment of the present invention.

For example FIG. 4 is a flowchart illustrating the operation of one embodiment of a stimulation device to detect and correct the undersensing of intrinsic cardiac electrical activity. In this flow chart, the various operational steps are summarized in individual "blocks". Such blocks describe specific actions or decisions that are carried out during operation of the illustrated device 10. Where a microcontroller (or equivalent) is employed, the flow chart presented herein provides the basis for a "control program" that may be used by such a microcontroller (or equivalent) to effectuate the desired control of the stimulation device.

In accordance with one embodiment of the present invention an implanted stimulation device 10 monitors cardiac signals from the patient to determine whether the device is undersensing intrinsic activity 400. As discussed above, the sensed signals may be amplified, filtered and sampled by the atrial and ventricular sensing circuits. The microcontroller processes the sensed cardiac signals to detect device undersensing 410.

In one embodiment the microcontroller may analyze two or more characteristics of the sensed cardiac signals (i.e. two or more atrial undersensing parameters) to detect device undersensing. For example, in one embodiment the microcontroller analyzes intrinsic cardiac activity on the atrial channel to initially detect atrial undersensing. The device may then analyze intrinsic activity on the ventricular channel to confirm the detection of atrial undersensing. Alternatively the microcontroller may analyze intrinsic activity on the atrial channel under current pacing parameters to initially diagnose atrial undersensing. The microcontroller then alters the current pacing parameters in the atrium and or ventricle while continuing to monitor intrinsic atrial activity to confirm the diagnosis of device undersensing.

In one embodiment of the present invention the detection of atrial undersensing may be combined with an automatic capability to adjust and otherwise optimize the pacing therapy provided by the implantable device to correct the detected undersensing. For example, if cardiac undersensing is detected, the microcontroller implements one or more diagnostic procedures to determine the cause of the undersensed activity 420. For example, in one embodiment the implantable device incrementally increases atrial sensitivity to search for under-sensed P-waves, i.e. P-waves with low-amplitudes.

Similarly, the microcontroller may activate a predetermined second detection threshold that is less than the initial detection threshold but higher than the noise floor to search for under-sensed P-waves. Alternatively, the microcontroller may shorten the post ventricular atrial blanking interval to search for undersensed P-waves that fall within the programmed blanking interval or initiate a threshold detection algorithm to automatically adjust the threshold level.

The microcontroller of the implantable device then adjusts one or more operating parameters to correct for the undersensing of intrinsic cardiac activity 430. Processing then returns to step 400 wherein the device again monitors intrinsic cardiac electrical activity.

Figure 5:
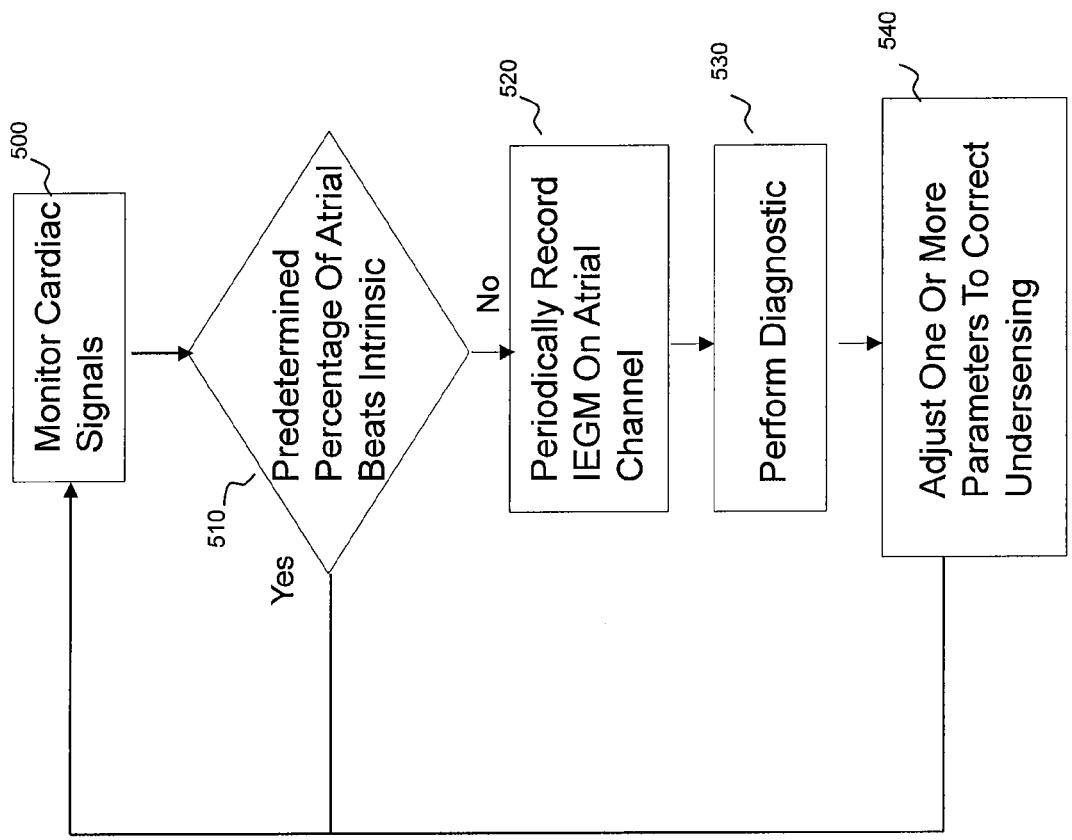
FIG. 5 is a flow chart illustrating a method to detect atrial undersensing as a function of intrinsic atrial electrical activity and for periodically recording an atrial IEGM for transmission to an external device in accordance with one embodiment of the present invention.

The present invention utilizes any of a variety of techniques to detect atrial undersensing. For example, FIG. 5 is a flowchart illustrating the operation of one embodiment of a stimulation device that monitors the frequency of occurrence of intrinsic atrial contractions to detect atrial undersensing. In this embodiment the implantable device monitors cardiac signals from the patient for a predetermined period of time to determine whether the device is undersensing intrinsic activity 500. The sensed signals may be amplified, filtered and sampled by the atrial and ventricular sensing circuits to detect intrinsic cardiac activity. In one embodiment the microcontroller stores in memory the numbered of paced and intrinsic beats as well as the number of premature atrial and ventricular contractions, i.e. PACs and PVCs respectively, or the like.

The microcontroller processes the sensed cardiac signals to detect intrinsic atrial activity, i.e. P-waves 510 during sustained periods of atrial pacing. If a predetermined percentage of the heart beats are intrinsic P-waves the device returns to monitoring cardiac signals. However, if a predetermined percentage of the heart beats are not intrinsic P-waves it is likely that the device is undersensing intrinsic atrial activity.

In this instance the microcontroller generates and stores one or more intracardiac electrograms (IEGMs) on a periodic basis 520 for transmission to an external device and follow up inspection for the presence of atrial fibrillation or other arrhythmias. In one embodiment the device explicitly annotates the IEGMs to alert the physician to the potential for atrial undersensing.

The implantable device also implements one or more diagnostic procedures to determine the cause of the undersensed activity 530. The implantable device then adjusts one or more operating parameters in accordance with the result of the diagnostic procedure to correct for the undersensing of intrinsic cardiac activity 540. Processing then returns to step 500 wherein the device again monitors intrinsic cardiac electrical activity.

Figure 6:
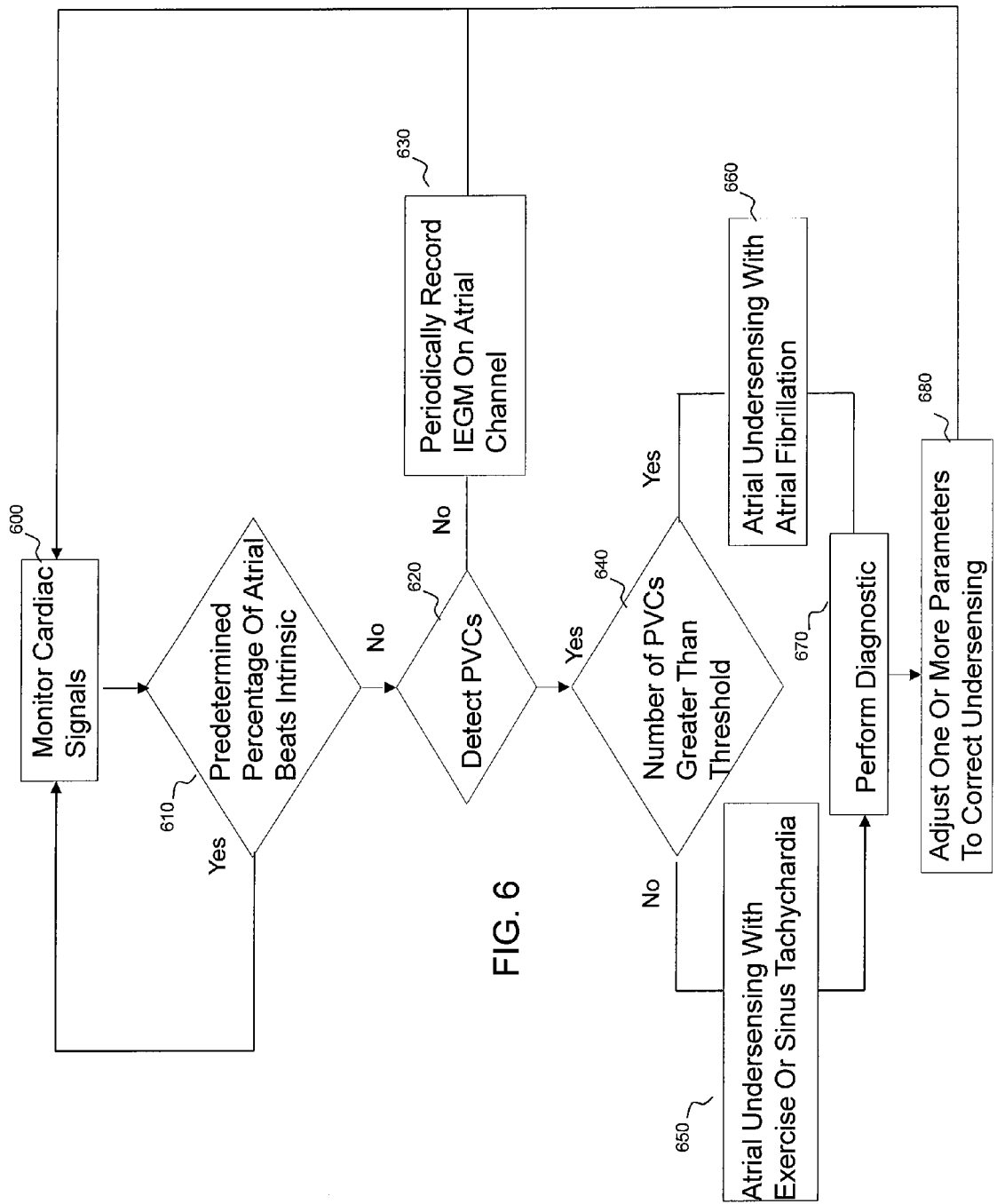
FIG. 6 is a flow chart illustrating a method to detect atrial undersensing as a function of intrinsic atrial activity and intrinsic ventricular activity in accordance with one embodiment of the present invention.

Alternatively, FIG. 6 is a flowchart illustrating the operation of another embodiment of a stimulation device that monitors cardiac signals from the patient for a predetermined period of time (or number of beats) to determine whether the device is undersensing intrinsic activity 600. The sensed signals may be amplified, filtered and sampled by the atrial and ventricular sensing circuits to detect intrinsic cardiac activity.

In one embodiment the microcontroller stores in memory the numbered of paced and intrinsic beats as well as the number of premature atrial and ventricular contractions, i.e. PACs and PVCs respectively including ventricular contractions having an interval between the preceding atrial beat and the intrinsic ventricular contraction that is less than a physiologic threshold (i.e. the A-R interval) for A-R events.

In some embodiments the patient's physician can program the physiologic threshold in accordance with the physiological needs of the individual patient. Alternatively, the microcontroller can automatically determine the physiologic program in accordance with any of a variety of physiological parameters measured by the device.

In this embodiment, the microcontroller again processes the sensed cardiac signals to detect intrinsic atrial activity, i.e. P-waves, and to determine the number of P-waves as a percentage of the total number of atrial beats 610 during periods of sustained atrial pacing. If a predetermined percentage of the heart beats are intrinsic P-waves the device returns to monitoring cardiac signals 600. However, if a predetermined percentage of the heart beats are not intrinsic P-waves it is likely that the device is undersensing intrinsic atrial activity. Alternatively, where there are no missed events the patient is likely suffering from sick sinus syndrome and the lack of intrinsic activity is again due to an improperly operating sinus node.

Therefore, in one embodiment, the microcontroller then determines if the patient has conduction between the atrium and ventricles. If the patient has in-tact ventricular conduction the microcontroller determines if one or more PVCs have been detected 620 to distinguish between device undersensing and sick sinus syndrome. If one or more PVCs have not been detected it is likely that the patient is suffering from sick sinus syndrome and the device stores an atrial intracardiac electrogram (IEGM) on a periodic basis 630 for transmission to an external device and follow-up inspection by the treating physician.

The presence of PVCs in a patient with an in-tact conduction system further indicates that intrinsic activity is not being detected by the device but is being conducted to the patient's ventricle, resulting in the random occurrence of ventricular contractions. In addition, if one or more PVCs have been detected the microcontroller determines whether the number of PVCs is greater than a predetermined threshold 640 to distinguish between possible episodes of sinus tachycardia and atrial fibrillation.

For example, in one embodiment if the number of PVCs is less than the predetermined threshold the microcontroller diagnosis atrial undersensing with accompanying sinus tachycardia or an elevated sinus rhythm due to exercise 650. In this embodiment the microcontroller activates, by way of example, a secondary sensor, such as for example, an activity detector, a minute ventilation sensor or the like, to determine the metabolic indicated rate and whether the patient is experiencing heightened physical activity to distinguish between sinus tachycardia and an elevated sinus rhythm due to exercise. If necessary the microcontroller then implements one or more therapeutic pacing therapies to terminate the detected tachycardia.

Alternatively, if the number of PVCs is greater than the predetermined threshold the microcontroller diagnosis atrial undersensing with accompanying atrial fibrillation 660. In this instance the microcontroller may implement one or more therapeutic pacing therapies to terminate the detected atrial fibrillation. The microcontroller may also generate diagnostic information documenting the occurrence and length of the sinus arrhythmia for transmission to an external device.

The microcontroller again implements one or more diagnostic procedures in response to the detection of atrial undersensing to determine the cause of the undersensed activity 670. The microcontroller then adjusts one or more operating parameters in accordance with the result of the diagnostic procedure to correct for the undersensing of intrinsic cardiac activity 680. Processing then returns to step 600 wherein the device again monitors intrinsic cardiac electrical activity.

Figure 7:
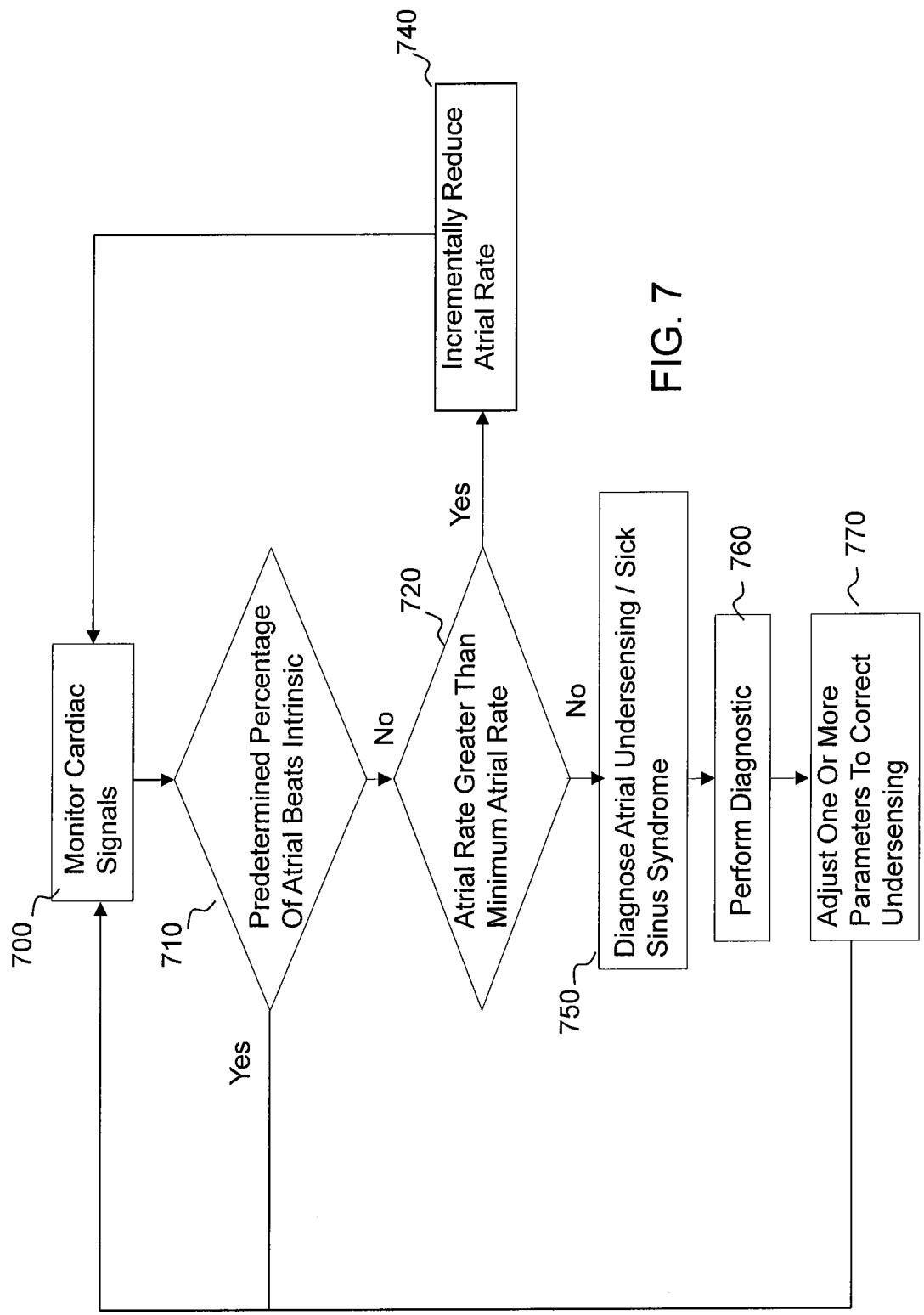
FIG. 7 is a flow chart illustrating a method to detect atrial undersensing as a function of intrinsic atrial activity during incremental reduction of the atrial pacing rate in accordance with one embodiment of the present invention.

FIG. 7 is a flowchart illustrating the operation of another embodiment of a stimulation device that also monitors cardiac signals from the patient for a predetermined period of time to determine whether the device is undersensing intrinsic activity 700. In this embodiment, the microcontroller again processes the sensed cardiac signals to detect intrinsic atrial activity, i.e. P-waves, and to determine the number of P-waves as a percentage of the total number of atrial beats 710. If a predetermined percentage of the heart beats are P-waves the microcontroller returns to monitoring cardiac signals 700. However, if a predetermined percentage of the heart beats are not P-waves it is likely that the device is undersensing intrinsic atrial activity or the patient is suffering from a malfunctioning sinus node.

Therefore, if a predetermined number of atrial beats are not intrinsic beats the microcontroller compares the atrial pacing rate with a minimum atrial pacing rate 720. If the current atrial pacing rate is greater than a minimum atrial rate the microcontroller incrementally reduces the atrial pacing rate 740 and returns to monitoring the cardiac signals for a predetermined time or predetermined number of total heart beats. The microcontroller again processes the sensed cardiac signals to detect intrinsic atrial activity, i.e. P-waves and to determine the number of P-waves as a percentage of the total number of atrial beats 710.

If a predetermined percentage of the heart beats are P-waves the microcontroller returns to monitoring cardiac signals 700. If a predetermined percentage of the heart beats are not P-waves the microcontroller repetitively determines if the current atrial rate is greater than the minimum atrial rate 720 and if so decreases the atrial rate 740 until a predetermined percentage of P-waves are detected or until the current rate is no longer greater than the minimum atrial rate yielding a diagnosis of device undersensing or sick sinus syndrome 750.

In this instance the microcontroller again implements one or more diagnostic procedures as previously described to determine the cause of the undersensing 760. The implantable microcontroller then adjusts one or more operating parameters in accordance with the results of the diagnostic procedure to correct for the undersensing of intrinsic cardiac activity 770 and returns to monitoring intrinsic cardiac electrical activity 700. Alternatively, if the diagnostic procedures do not detect a pacing or sensing parameter that is the cause of the undersensing the patient is likely suffering from a malfunctioning or inoperable sinus node.

Figure 8:
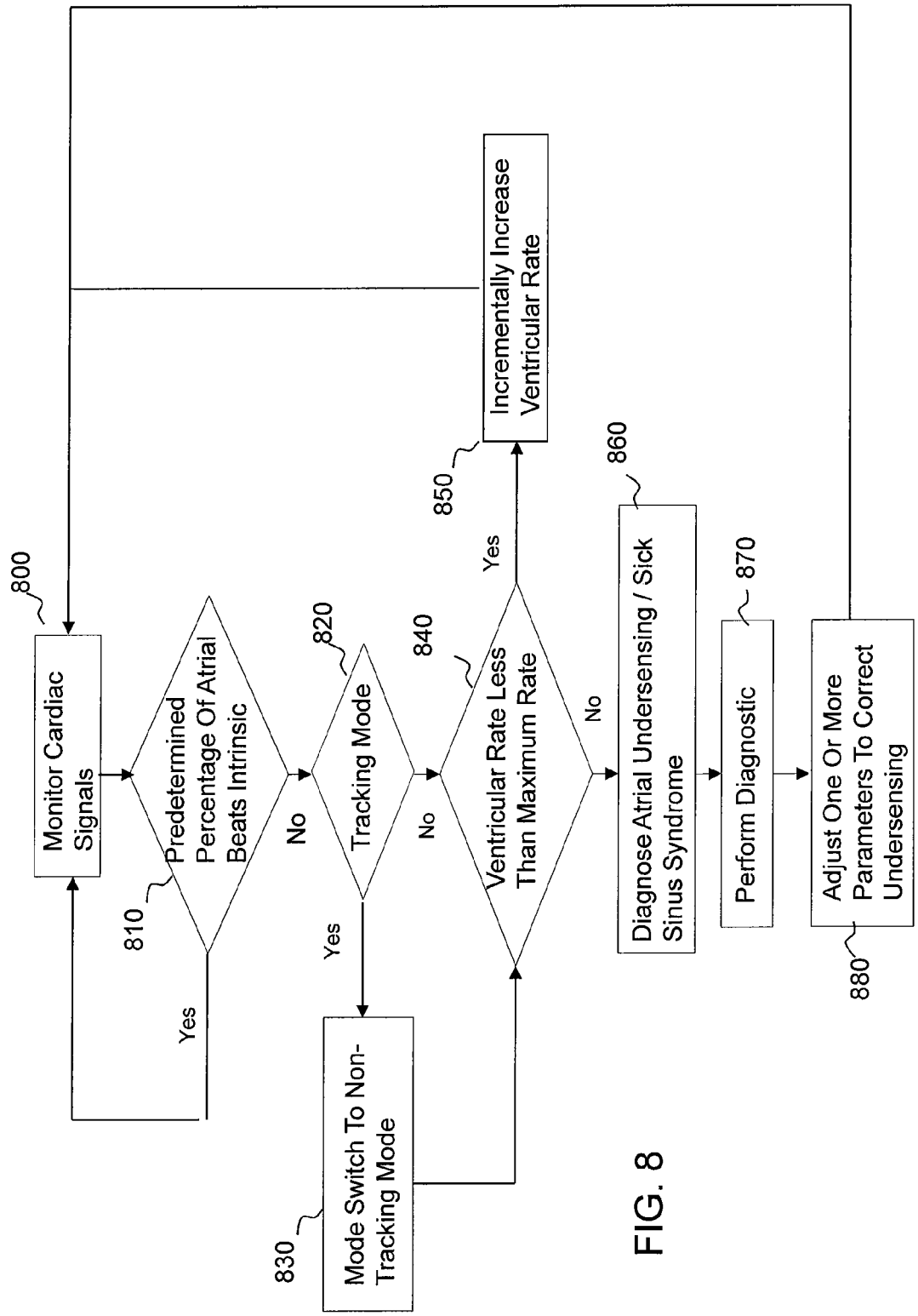
FIG. 8 is a flow chart illustrating a method to detect atrial undersensing as a function of atrial intrinsic activity while increasing the ventricular pacing rate in accordance with one embodiment of the present invention.

FIG. 8 is a flowchart illustrating the operation of another embodiment of a stimulation device that also monitors cardiac signals from the patient for a predetermined period of time to determine whether the device is undersensing intrinsic activity 800. In this embodiment, the microcontroller again processes the sensed cardiac signals to detect intrinsic atrial activity, i.e. P-waves, and to determine the number of P-waves as a percentage of the total number of atrial beats 810. If a predetermined percentage of the heart beats are P-waves the device returns to monitoring cardiac signals 800.

In this embodiment, if a predetermined number of atrial beats are not intrinsic beats the device determines if the current pacing mode is a tracking mode (e.g. DDDR) 820. If the current pacing mode is a tracking mode the microcontroller switches to a non-tracking pacing mode 830. The microcontroller may then adjust the ventricular pacing rate to ensure that ventricular pacing is not interfering with atrial channel sensing.

For example, in one embodiment the microcontroller compares the ventricular pacing rate with a maximum ventricular pacing rate 840. If the current ventricular pacing rate is less than the maximum ventricular rate the microcontroller incrementally increases the ventricular pacing rate 850 and returns to monitoring cardiac signals for a predetermined time or predetermined total number of heart beats 800.

The microcontroller again processes the sensed cardiac signals to detect intrinsic atrial activity and to determine the number of P-waves as a percentage of the total number of atrial beats 810. If a predetermined percentage of the heart beats are P-waves the microcontroller returns to monitoring cardiac signals 800.

If a predetermined percentage of the heart beats are not P-waves the microcontroller repetitively determines if the current ventricular rate is less than the maximum ventricular rate 820 and if so increases the ventricular rate 850 until a predetermined percentage of P-waves are detected or until the current rate is no longer less than the maximum ventricular rate yielding a diagnosis of atrial undersensing or sick sinus syndrome.

The microcontroller in some embodiments monitors atrial electrical activity to detect retrograde grade conduction of paced events in the ventricle to the atrium. In these embodiments the microcontroller may reduce the ventricular pacing rate if retrograde contractions are detected.

One of skill in the art will appreciate that the ventricular rate may be varied in variety of known techniques to determine if ventricular pacing is interfering with atrial sensing. For example, in other embodiments the microcontroller will determine if the current ventricular pacing rate is greater than a minimum pacing rate as programmed by the physician or determined by the device and decreases the ventricular rate if the current rate is greater than the minimum rate. Alternatively, the micro-controller may dither the ventricular pacing rate around the current pacing rate in accordance with a predetermined schedule.

In response to the initial detection of atrial undersensing 860 the microcontroller again implements one or more diagnostic procedures to determine the cause of the device undersensing 870. The implantable device then adjusts one or more operating parameters in accordance with the results of the diagnostic procedure to correct for the undersensing of intrinsic cardiac activity 880 then returns to monitoring intrinsic cardiac electrical activity 800.

In one embodiment of the present invention the implantable medical device includes one or more automatic mode switch algorithms wherein the pacemaker reverts from a tracking mode such as a VDD or DDD mode, to a non-tracking mode such as WI or DDI mode in response to the detection of an atrial tachyarrhythmia. DDD, WI and DDI are standard device codes which identify the mode of operation of the device.

DDD indicates a device which senses and paces in both the atria and the ventricles and is capable of both triggering and inhibiting functions based upon sensed events. WI indicates that the device is capable of pacing and sensing only within the ventricle and is only capable of inhibiting the functions based upon sensed events. DDI is identical to DDD except that the device is only capable of inhibiting functions based upon sensed events, rather than triggering functions. Numerous other device modes of operation are possible, each represented by standard abbreviations of this type.

During tracking mode operation a sensed event on the atrial channel triggers a ventricular output after a programmable delay. The tracking of high atrial rates increases the likelihood that the device will deliver a ventricular pulse during a vulnerable period (i.e. on a T-wave) when the ventricle is not completely refractory, possibly inducing a ventricular tachycardia.

However, in single chamber operational modes, high atrial rates are not tracked by the ventricular output, i.e. ventricular outputs are not triggered in response to sensed atrial events thereby preventing the induction of a ventricular tachycardia during episodes of atrial tachycardia. Therefore, switching to a non-tracking mode in response to the detection of an atrial tachycardia reduces the likelihood that the device will induce an episode of ventricular tachycardia.

Figure 9:
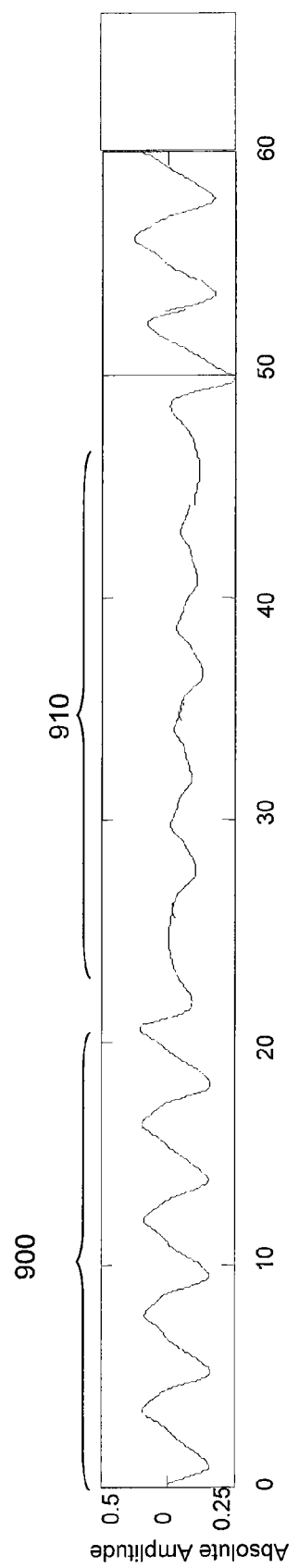
FIG. 9 is a representative IEGM graphically illustrating the amplitude of intrinsic atrial cardiac activity during atrial fibrillation.

However, as illustrated in FIG. 9, the amplitude of the signals sensed on the atrial channel tends to wax and wane during periods of atrial fibrillation which is characterized by rapid and chaotic electrical impulses in the atria. This waxing and waning of the amplitude of the fibrillation potentials can result in intermittent sensing of a long standing atrial fibrillation event, causing it to be diagnosed as numerous short duration runs of atrial tachycardia.

Therefore atrial fibrillation often results in frequent mode switches as the device tracks the atrial channel during episodes of high amplitude signals 900 and switches to a non-tracking mode due to detection of an atrial tachycardia. The device may however incorrectly return to a tracking mode during an episode of atrial fibrillation because the device undersenses atrial activity during low amplitude periods 910 of the atrial fibrillation episode.

Figure 10:
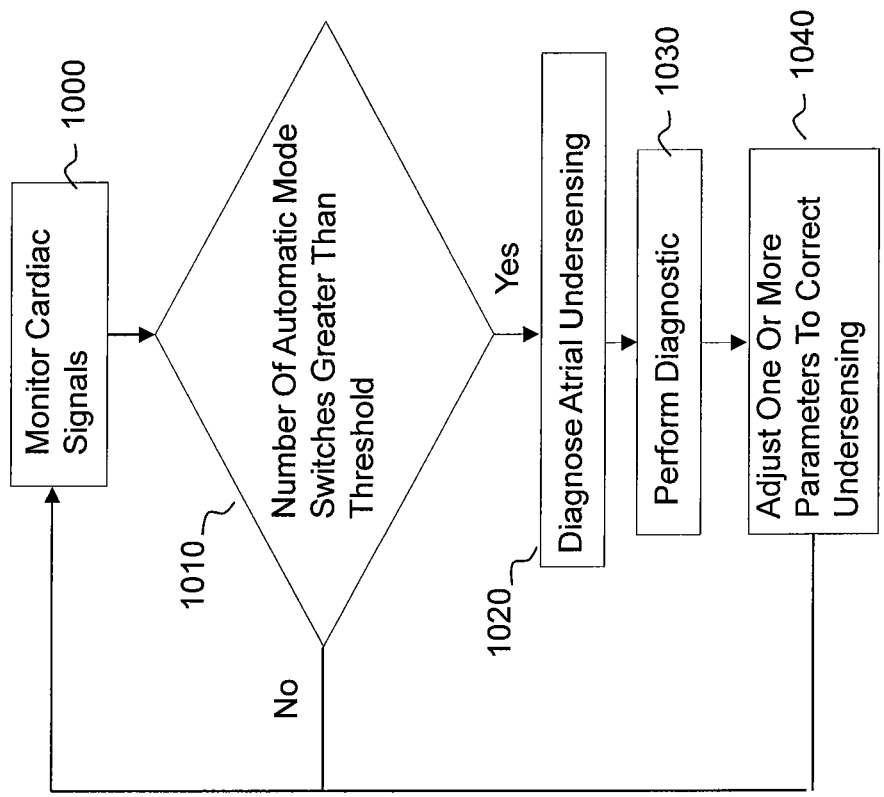
FIG. 10 is a flow chart illustrating a method to detect atrial undersensing as a function of the number of automatic mode switches from a tracking mode to a non-tracking mode in accordance with one embodiment of the present invention.

Therefore, as illustrated in the flow chart of FIG. 10, in one embodiment of the present invention the microcontroller monitors the number of automatic mode switches during a predetermined time period 1000. In this embodiment the device periodically compares the number of mode switches to a predetermined threshold 1010. If the number of mode switches from tracking mode to non-tracking mode and back to a tracking mode exceeds a predetermined threshold it is likely the patient is in atrial fibrillation and the device is undersensing intrinsic activity on the atrial channel and the microcontroller diagnoses atrial undersensing 1020.

In this embodiment the microcontroller again implements one or more diagnostic procedures to determine the cause of the device undersensing 1030. The microcontroller then adjusts one or more operating parameters of the implantable device in accordance with the results of the one or more diagnostic procedures to correct for the undersensing of intrinsic cardiac activity 1040 and then returns to monitoring intrinsic cardiac electrical activity 1000. One of skill in the art will appreciate that this embodiment may also monitor the number of intrinsic beats as a percentage of the total number of heart beats to either trigger the automatic mode switch analysis or to confirm the diagnosis drawn from that analysis.

In another embodiment of the present invention the microcontroller includes detection circuitry, for detecting an evoked response from the heart in response to an applied stimulus, thereby aiding in the detection of "capture". Capture occurs when an electrical stimulus applied to the heart is of sufficient energy to depolarize the cardiac tissue, thereby causing the heart muscle to contract. The consistent detection of an evoked response in response to applied stimulation pulses indicates that the heart was refractory when the stimulus was applied suggesting that atrial undersensing has not occurred.

Figure 11:
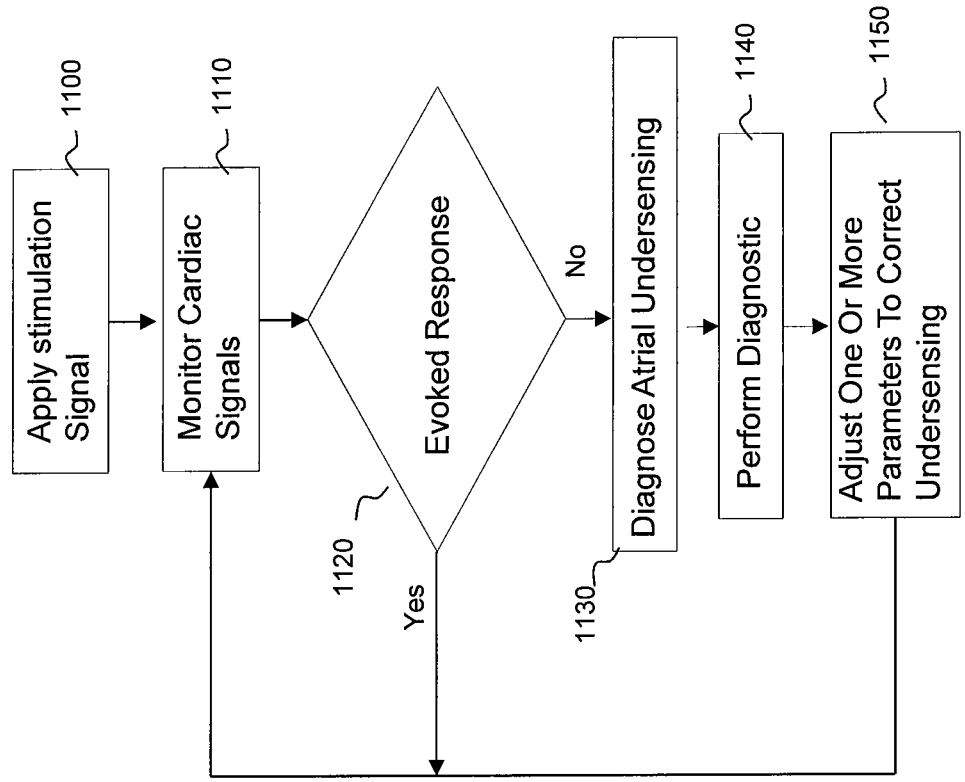
FIG. 11 is a flow chart illustrating a method to detect atrial undersensing as a function of the detection of an evoked response corresponding to one or more atrial pacing pulses in accordance with one embodiment of the present invention.

Therefore, in one embodiment the microcontroller monitors cardiac signals 1110 to detect an evoked response following a stimulation pulse 1100 as illustrated in the flow chart of FIG. 11. In one embodiment the microcontroller enables capture or evoked response detection by triggering the atrial pulse generator to generate a stimulation pulse, starting a capture detection window using timing control circuitry within the microcontroller, and enabling the data acquisition system to sample the cardiac signal that falls in the capture detection window. The microcontroller then analyzes the amplitude, morphology or other parameters of the cardiac signal to determine if an evoked response (i.e. capture) has occurred 1120.

Evoked response detection may occur on a beat-by-beat basis for a predetermined number of beats or on a sampled basis. The evoked response detection algorithm can be invoked periodically as a test for atrial undersensing or may be triggered by the failure to detect a predetermined percentage of intrinsic beats as previously described. If an evoked response is detected for each stimulation pulse, the microcontroller returns to monitoring cardiac signals.

If an evoked response is not detected after each stimulation pulse or if a predetermined percentage of evoked responses are not detected after a predetermined number of pulses the microcontroller concludes that atrial undersensing has occurred 1130 and implements one or more diagnostic procedures to determine the cause of the device undersensing 1140. The microcontroller then adjusts one or more operating parameters of the implantable device in accordance with the results of the diagnostic procedures to correct for the undersensing of intrinsic cardiac activity 1150 and then returns to monitoring intrinsic cardiac electrical activity.

Figure 12:
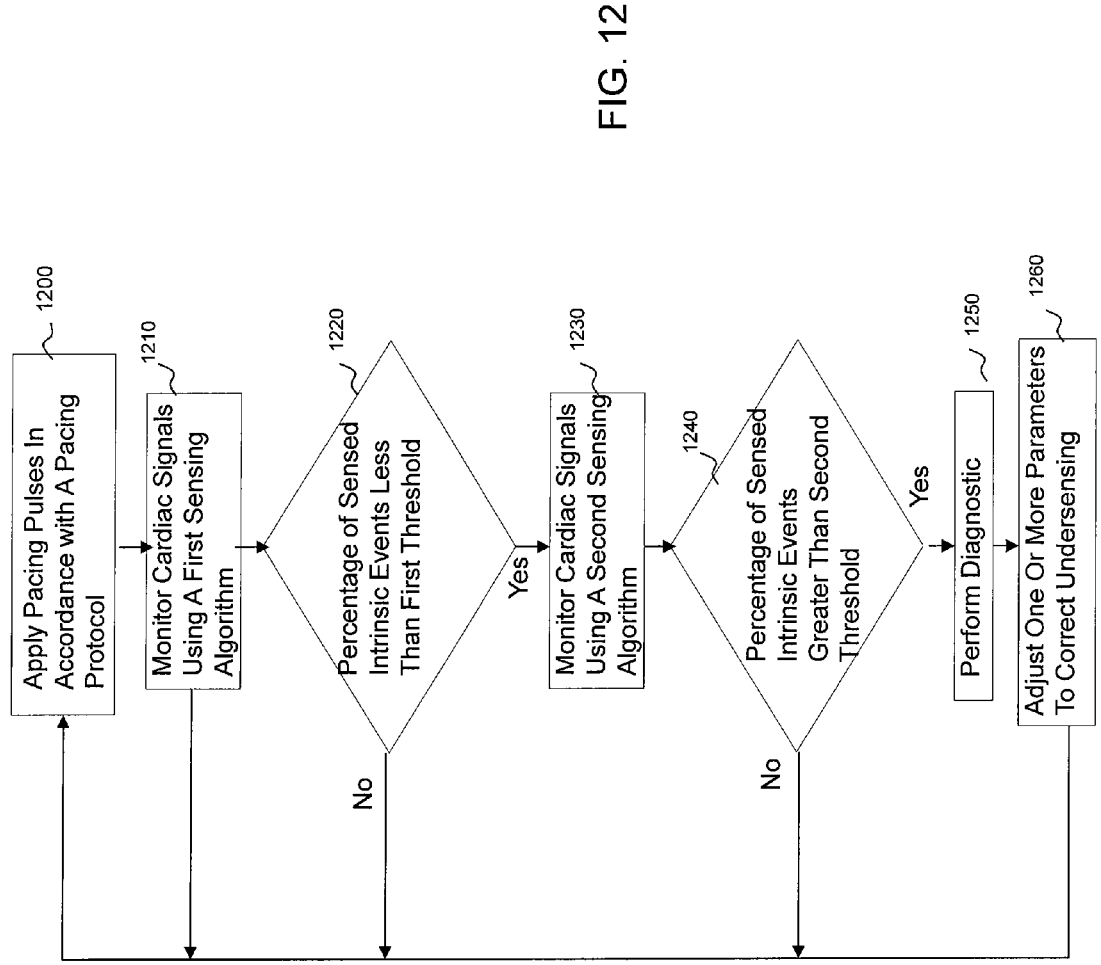
FIG. 12 is a flow chart illustrating a method to detect atrial undersensing utilizing multiple sensing algorithm in accordance with one embodiment of the present invention.

In accordance with another embodiment of the present invention an implanted stimulation device 10 delivers cardiac pacing pulses to one or more atria of a patient's heart in accordance with a pacing protocol 1200 as illustrated in the flow chart of FIG. 12. As is known in the art, various pacing protocols provide for pacing and sensing in various chambers of the heart as well as various modes of tracking and responding to electrical activity sensed in one or more chambers of the heart.

In this embodiment, the microcontroller monitors cardiac signals from the patient in accordance with a first sensing algorithm as necessary for the operation of the pacing protocol 1210. For example, a sensed intrinsic event in a chamber of the patient's heart can be used to inhibit the delivery of a pacing pulse to that chamber of the heart. The detection of an intrinsic pulse may also be used for various other purposes known in the art, such as for triggering various intervals which are used to time the delivery of pacing pulses to other chambers of the heart.

In one embodiment the micro-controller monitors the frequency of occurrence of intrinsic contractions between paced beats using the first sensing algorithm. The lack of a predetermined percentage of sensed beats between paced beats provides an indication that the device might be undersensing intrinsic activity.

In some embodiments the micro-controller also operates a second sensing algorithm to monitor sensed cardiac signals to provide for the detection of undersensing of intrinsic cardiac activity 1230 if the percentage of sensed intrinsic beats is less than a first threshold 1220. Otherwise the device returns to delivering pacing pulses to one or more atria of the patient's heart.

One of skill in the art will appreciate that other indications of possible undersensing may also be tracked and utilized to trigger the secondary sensing algorithm. Alternatively, in some embodiments the microcontroller may continuously operate the second sensing algorithm in parallel with the first sensing algorithm to provide continuous verification of the adequacy of the pacing protocol parameters.

The second sensing algorithm may implement any of a variety of known techniques for detecting intrinsic cardiac activity. For example, in one embodiment the microcontroller activates a second atrial sensing threshold having an amplitude between a first atrial sensing threshold used to support the pacing protocol and a noise floor. Alternatively, the second sensing algorithm may compare the morphology of the sensed complex to a stored template to detect undersensed intrinsic activity. Similarly, the second sensing algorithm may analyze the frequency content of the sensed complex to detect intrinsic activity.

If a predetermined percentage of the heart beats detected with the second sensing algorithm are intrinsic beats (e.g. P-waves) the device detects cardiac undersensing 1240. Otherwise the device returns to monitoring cardiac signals.

The microcontroller may again generate and store one or more intracardiac electrograms (IEGMs) in response to the detection of undersensing for transmission to an external device and follow up inspection for the presence of atrial fibrillation or other arrhythmias (not specifically shown). In one embodiment the device explicitly annotates the IEGMs to alert the physician to the potential for atrial undersensing.

The implantable device may again implement one or more diagnostic procedures to determine the cause of the undersensed activity 1250. The implantable device then adjusts one or more operating parameters in accordance with the result of the diagnostic procedure to correct for the undersensing of intrinsic cardiac activity 1260 and returns to delivering pacing pulses using the adjusted operating parameters.

While the invention herein disclosed has been described by means of specific embodiments and applications thereof, numerous modifications and variations could be made thereto by those skilled in the art without departing from the scope of the invention set forth in the claims. For example, the methods or algorithms described in connection with the embodiments disclosed herein may be embodied directly in hardware, in a software module executed by a processor, or in a combination of the two.

A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for operating an implantable medical device, comprising:
   monitoring intrinsic atrial activity to detect intrinsic atrial contractions between one or more of a plurality of atrial pacing pulses;
   detecting atrial undersensing as a function of intrinsic atrial electrical activity; and
   confirming detection of atrial undersensing as a function of intrinsic ventricular electrical activity.

2. The method of claim 1 wherein confirming detection of atrial undersensing as a function of intrinsic ventricular electrical activity comprises confirming detection of atrial undersensing as a function of detection of one or more premature ventricular contractions.

3. A method for operating an implantable medical device, comprising:
   detecting atrial undersensing as a function of detection of intrinsic atrial electrical activity when pacing with a set of pacing parameters;
   adjusting one or more of the set of pacing parameters; and
   confirming detection of atrial undersensing as a function of detection of intrinsic atrial electrical activity while pacing in accordance with the adjusted pacing parameters.

4. The method of claim 3 wherein adjusting one or more of the set of pacing parameters comprises incrementally reducing an atrial pacing rate and wherein confirming detection of atrial undersensing comprises detecting atrial undersensing as a function of detection of intrinsic atrial electrical activity while pacing in accordance with the reduced atrial pacing rate.

5. The method of claim 3 further comprising performing one or more diagnostic procedures to determine the cause of the undersensed atrial activity.

6. The method of claim 3 further comprising increasing sensitivity on an atrial channel to eliminate atrial undersensing.

7. The method of claim 3 further comprising activating a second atrial sensing threshold having an amplitude between a current atrial sensing threshold and a noise floor to eliminate atrial undersensing.

* * * * *